(12) United States Patent
Murphy

(10) Patent No.: US 7,846,092 B2
(45) Date of Patent: Dec. 7, 2010

(54) SURGICAL RETRACTOR WITH IMPACTOR

(75) Inventor: Stephen B. Murphy, Winchester, MA (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 11/744,523

(22) Filed: May 4, 2007

(65) Prior Publication Data

US 2007/0260122 A1  Nov. 8, 2007

Related U.S. Application Data

(60) Provisional application No. 60/746,547, filed on May 5, 2006.

(51) Int. Cl.
*A61B 1/32* (2006.01)
(52) U.S. Cl. .................................... 600/201
(58) Field of Classification Search ............. 600/201, 600/210, 211
See application file for complete search history.

(56) References Cited

U.S. PATENT DOCUMENTS

| 5,303,694 | A | * | 4/1994 | Mikhail ..................... 600/214 |
| 6,083,225 | A | * | 7/2000 | Winslow et al. ........... 606/86 A |
| 2002/0123668 | A1 | * | 9/2002 | Ritland ....................... 600/210 |
| 2005/0154395 | A1 | * | 7/2005 | Robbins et al. ............ 606/90 |

* cited by examiner

*Primary Examiner*—Todd E Manahan
*Assistant Examiner*—Elana B Fisher

(57) ABSTRACT

A surgical retractor comprising a retractor body having a site portion and a handle portion, and an impactor body on the retractor body. The impactor body is positioned and configured for use in impacting the site portion in the surgical site. An impaction axis of the impaction body is preferably substantially aligned with an axis of the site portion of the impactor body. The impactor body is preferably attached to the retractor body at a junction between the site portion and the handle portion of the retractor body. In one embodiment, the impactor portion is configured to selectively mate with an impactor extension member to thereby optionally receive direct impaction on the impactor portion or indirect impaction through the impactor extension member.

7 Claims, 3 Drawing Sheets

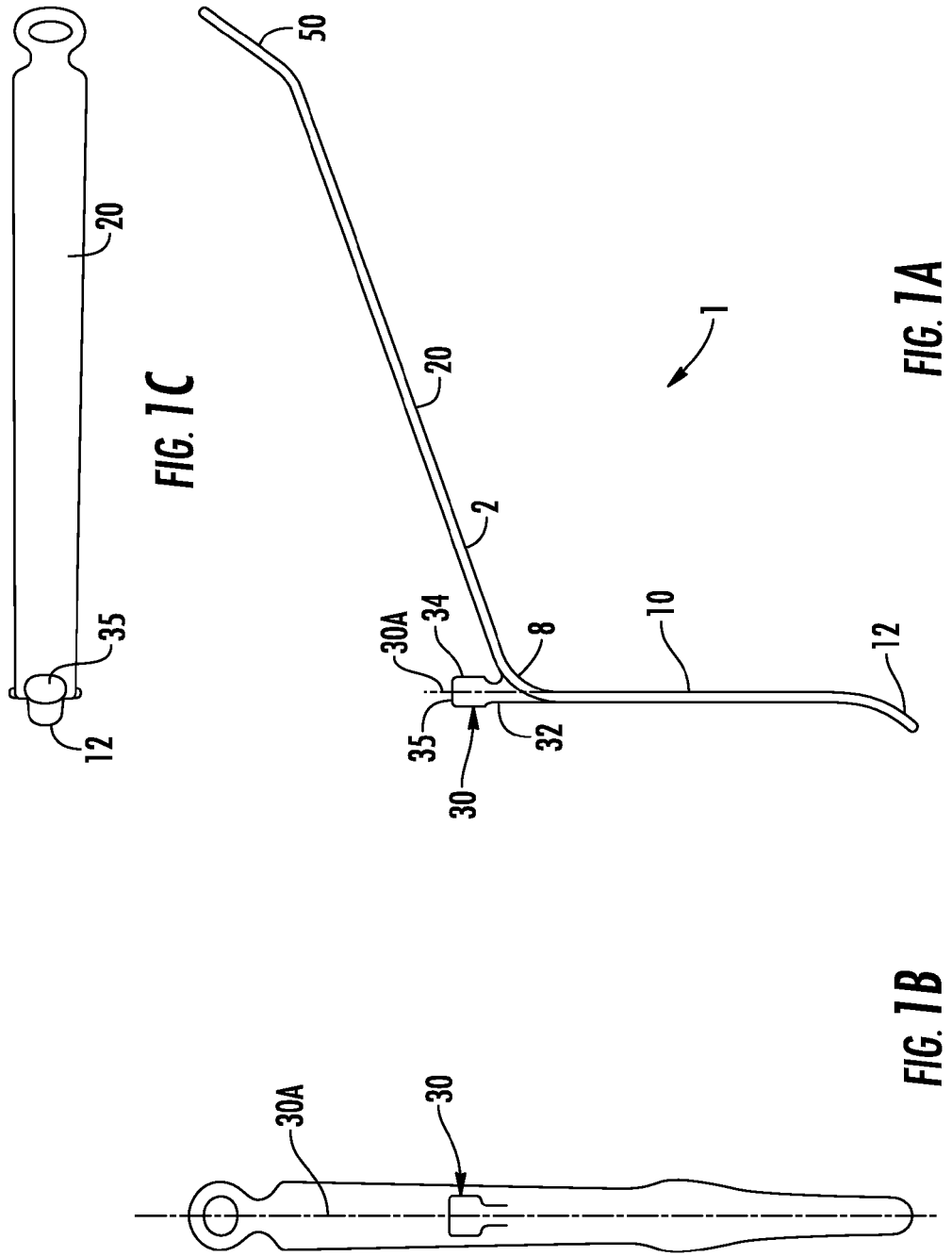

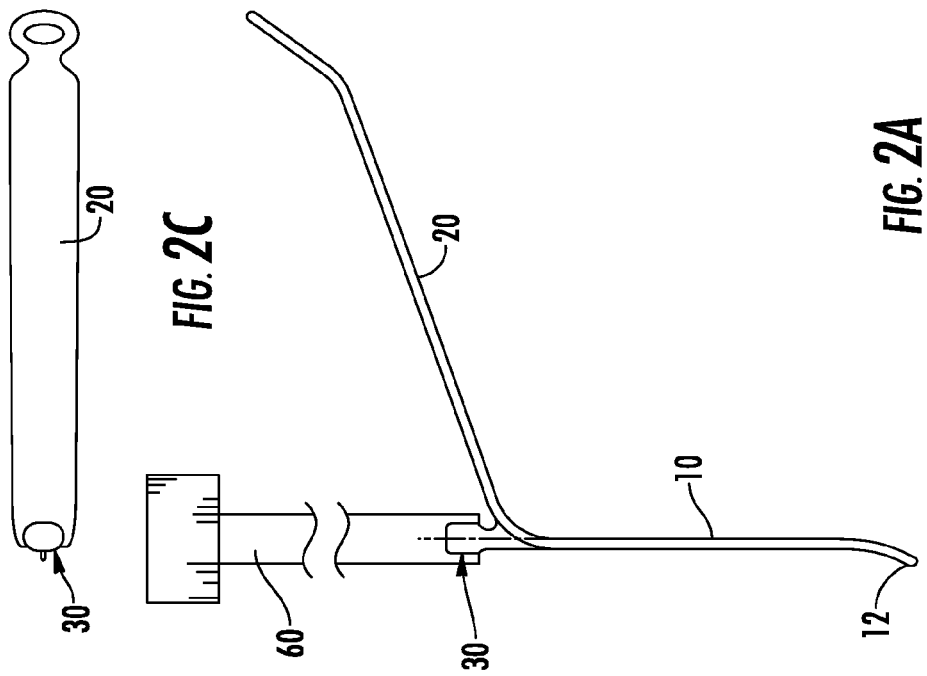
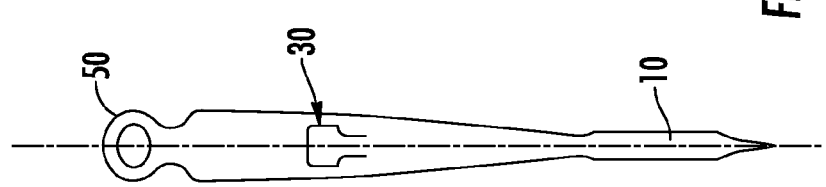

SURGICAL RETRACTOR WITH IMPACTOR

CROSS REFERENCE TO RELATED APPLICATIONS

This application claims priority to U.S. Provisional Patent Application 60/746,547, filed on May 5, 2006, which is pending and which is incorporated herein by reference.

STATEMENT REGARDING FEDERALLY SPONSORED RESEARCH

Not applicable

REFERENCE TO A MICROFICHE APPENDIX

Not applicable

FIELD OF THE INVENTION

The present invention relates to orthopedic surgery, and more particularly to retractors adapted particularly for use in minimally invasive surgery procedures, such as in the hip.

BACKGROUND OF THE INVENTION

In surgical procedures, retractors are used to retract tissue in an incision, and thereby open the incision for use in carrying out the surgical procedure. Leverage retractors that use a fulcrum around a tissue structure (typically, bone) or that create a fulcrum by placing the tip of the retractor into the bone are vital and commonly used in surgery in general, and in orthopedic surgery in particular. Retractors that are fairly straight can be driven into the bone or through a soft-tissue interval by using a mallet to impact the retractor into the desired location. Curved or bent retractors, on the other hand, are preferred for many procedures because the handle end of the retractor can be placed farther from the incision, which provides a better lever-arm and keeps hands or holders farther from the incision and sharp instruments. Curved or bent retractors are also less likely to obstruct the surgeon's view during surgery. Unfortunately, bent retractors are difficult to impact because the impacting end of the retractor creates a force in the wrong direction.

Impactors are commonly used in surgical procedures to transfer an impaction force to a particular instrument or implant. For example, in hip arthroplasty, impactors are used to impact acetabular shells into a prepared acetabulum. In the past, bent retractors have been designed with a fenestration near the working tip of the retractor so that a retractor-impactor can be placed in the fenestration such that the use of a mallet will provide a force in the correct direction for retractor impaction. Unfortunately, these retractor-impactor combinations are awkward to use since they require three hands to manage: one to control the impactor; one to control the retractor; and one to control the mallet.

In recent years, efforts have been made to develop instruments and procedures for use in minimally invasive surgery, and minimally invasive hip and knee arthroplasty in particular. In minimally invasive surgery ("MIS"), the operation is carried out through a small incision, such as an 8 cm incision, for example. MIS procedures may reduce trauma to the patient's muscles and other tissues, and typically result in shorter patient recovery time. However, operating in the confines of a small incision presents challenges to the surgeon. The surgeon must often rely on specialized surgical instruments in order to access or operate within the surgical site. While performing MIS hip procedures, the inventor, who is an experienced orthopedic surgeon, discovered the need for a retractor of the type described herein.

OBJECTS AND SUMMARY OF THE INVENTION

It is an object of the invention to provide an improved means of positioning and securing a retractor in a surgical site.

It is another object of the invention to provide improved means of impacting a retractor.

It is another object of the invention to provide a retractor having an impactor that is particularly adapted for use in MIS hip procedures.

The foregoing and other objects of the invention are achieved by providing a surgical retractor for use in a surgical site comprising a retractor body having a site portion and a handle portion, and an impactor body on the retractor body. The impactor body is positioned and configured for use in impacting the site portion in the surgical site. The impactor body preferably includes an impactor portion having an impaction surface and a support portion, the impactor body being affixed to the retractor body via the support portion. The support portion of the impactor body is fixedly attached to the retractor body. An impaction axis of the impaction body is preferably substantially aligned with an axis of the site portion of the impactor body. The impactor body is preferably attached to the retractor body at a junction between the site portion and the handle portion of the retractor body. In one embodiment, the impactor portion is configured to selectively mate with an impactor extension member to thereby optionally receive direct impaction on the impactor portion or indirect impaction through the impactor extension member.

The retractor of the current invention advances the state of the art by placing, in a preferred embodiment, an impaction surface at the angle where the retractor bends. This improvement to the retractor allows bent retractors to be driven into the correct position using two hands, rather than three: one hand to control the retractor, and another to control the mallet.

The current invention still further advances the art in cases where the impaction surface lies too close to the skin to allow a mallet to be used safely directly against the impaction surface. The impaction surface is preferably further designed in a shape that, when mated with a corresponding retractor-impactor (a.k.a. impactor extension member), the retractor and retractor-impactor form a stable structure that can be controlled with one hand, thus retaining the ability to impact the retractor into the correct position using only two hands. In a preferred embodiment of the invention, the retractor-impactor fits onto and over the impaction surface so that about 5 or 6 degrees of freedom are controlled by the mating mechanism. In this way, without having to rigidly clamp the two parts together, the surgeon can simply slide the retractor-impactor onto the impaction surface along the long axis of the retractor-impactor. Thus, after the retractor is successfully impacted, the retractor-impactor can be withdrawn by sliding it off of the impaction surface without having the disconnect a rigid junction.

The design of an impaction surface on a bent retractor and the design of a retractor-impaction mating junction that can be controlled with one hand represent very significant advances of the current state of the art.

The foregoing and other objects, features, aspects and advantages of the invention will become more apparent from the following detailed description of the invention when considered in conjunction with the accompanying drawings.

BRIEF DESCRIPTION OF THE DRAWINGS

FIGS. 1A-1C provide side, front and top views of one preferred embodiment of the invention.

FIGS. 2A-2C provide side, front and top views of one preferred embodiment of the invention.

PREFERRED EMBODIMENTS OF THE INVENTION

Figure 3C:
FIGS. 3A-3C provide side, front and top views of one preferred embodiment of the invention.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

As shown in FIG. 1, the retractor 1 of the invention comprises, generally, a retractor body 2 having a site portion 10 and a handle portion 20, and an impactor body 30 on the retractor body 2. The impactor body 30 is positioned and configured for use in impacting the site portion 10 in the surgical site. A blow delivered to the impaction surface 35 transfers force generally along the axis of the site portion 10, as will be described in further detail below. A leading end 12 of the site portion 10 is curved or otherwise configured to provide sufficient anchorage and leverage against body tissue (such as against the acetabular rim) during retraction, in a manner known to those of skill in the art. As indicated in FIG. 1, a trailing end of the retractor body 2 is preferably provided with a butt portion 50, which is preferably angled and ring shaped in the manner of the prior art, for use in a manner known to those of skill in the art. The retractor 1 is preferably of unibody construction.

Figure 3A:
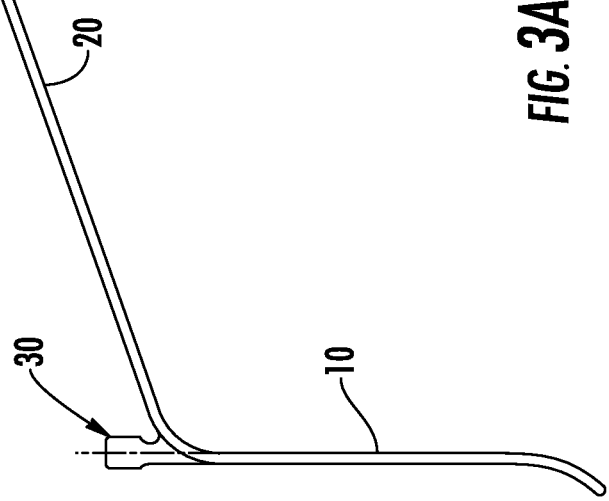
Figure 3B:
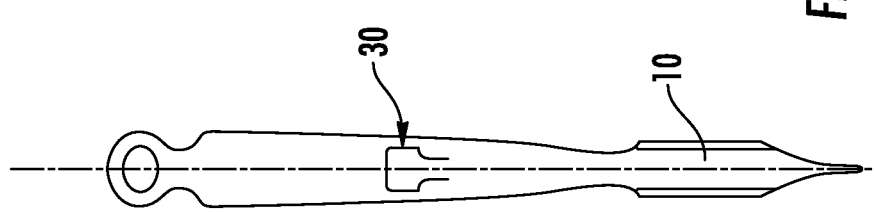

As shown in FIGS. 1-3, the impactor body 30 preferably includes an impactor portion 34 having an impaction surface 35 and a support portion 32. The impactor body 30 is affixed to the retractor body 2 via the support portion 32. The support portion 32 of impactor body 30 is preferably fixedly attached to the retractor body 2. As shown in FIG. 1B, an impaction axis 30A of the impaction body 30 is preferably substantially aligned with an axis of the site portion 10 of the impactor body 2, such that impaction blows delivered directly to the impaction surface 35 are transferred efficiently through the site portion 10.

As shown in FIG. 1A, the impactor body 30 is preferably attached to the retractor body 2 at a junction 8 between the site portion 10 and the handle portion 20 of the retractor body 2. In the embodiment of FIG. 1A, the junction 8 is bent in the manner of a conventional Hohman retractor. However, if the concepts of the invention were applied to retractors other than Hohman retractors, the impactor body 30 could be located at a different part of the retractor body 2.

As indicated in FIG. 2A, the impactor portion 34 is preferably configured to selectively mate with an impactor extension member (a.k.a. retractor-impactor) 60. As indicated in FIG. 2A, the impactor extension member 60 is preferably provided with a female leading end and an impactor surface on a trailing end. With the impactor extension member 60 mated to the impactor body 30 in the manner shown in FIG. 2A, impaction blows, such as with a conventional impaction mallet (not shown) are delivered directly to the impaction end of the impactor extension member 60, and the impaction force is transferred through the impactor extension member 60 and received indirectly by the impactor body 30 of the retractor 1. As indicated in FIG. 2A, the impactor portion 34 and the impactor extension member 60 are preferably configured to mate such that an impaction axis of the impactor body 30 and an impaction axis of the extension member 60 are substantially axially aligned. As noted above, this feature allows the combined retractor-impactor extension member to be used in a two hand, rather than three hand, procedure.

As indicated in FIG. 1C, the impactor portion 34 preferably has a non-circumferential or non-cylindrical configuration, such as an oval shape. In the ovoid embodiment of FIG. 1C, a lengthwise axis of the oval shape of the impaction surface 35 is preferably substantially parallel to a widthwise dimension of the site portion 10, which serves to minimize the amount, if any, of the impactor portion 34 that protrudes beyond the leading edge of the site portion 10. The non-circumferential configuration of the impactor portion 34 is configured to mate with the impactor extension member 60 in a non-rotating relationship, such that preferably about 5 or 6 degrees of freedom of motion are controlled at the junction. Due to the non-rotating relationship, the impactor extension 60 can be used to orient the site portion 10 of the retractor from outside of the incision, such that only one of the surgeon's hands is required to firmly control both instruments. This feature is important in MIS hip procedures, where it is sometimes difficult to maneuver the site portion 10 and the leading end 12 of the site portion 10 of a convention retractor into a desired position in the incision, such as against the rim of the acetabulum. The surgeon may find it useful to tap on the extension portion to assist in positioning and orienting the site portion 10. Once the site portion 10 is properly positioned, the surgeon can either impact the impactor extension member 60 or remove the impactor extension member 60 and impact directly on the impactor body 30 of the retractor 1.

Alternatively, an opposite type of impactor extension junction can be used, such as a small oblong female slot (slot) in the retractor and an impactor extension member having a leading end configured to fit the oblong slot. This type of configuration is useful in cases where a protruding impactor body 30 or impactor portion 34 gets in the way (such as in tight MIS conditions). In some embodiments, the impactor body 30 would be in an oblong male configuration with no real impaction surface, just an impaction receptacle.

In the embodiments shown in FIGS. 1-3, the surgical retractor 1 is sized and configured for use in minimally invasive procedures, and especially minimally invasive hip procedures. The drawings are shown to scale and in proportion.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A surgical retractor for use in a surgical site in hip surgery comprising:

a retractor body having a site portion and a handle portion, and a separate impactor extension member, said separate impactor extension member comprising a unibody solid impaction structure having a female leading end, an impactor surface on a trailing end, and a lengthwise straight portion extending between said leading end and said trailing end, said female leading end configured to receive an impaction surface of said retractor body, an impactor body on said retractor body, said impactor body positioned and configured for use in impacting said site portion in the surgical site, said impactor body including an impactor portion having an impaction surface and a support portion, said impactor body fixedly attached to said retractor body via said support portion, said impactor body attached to said retractor body at a junction between said site portion and said handle portion of said retractor body, said impactor portion having an oval shape configured to selectively mate with said impactor extension member to thereby optionally receive direct impaction on said impaction surface of said impactor portion or indirect impaction through said impactor extension member, as well as to enable manipulation of said site portion via said impactor extension member, a lengthwise axis of said oval shape substantially parallel to a widthwise dimension of said site portion, and an impaction axis of said impaction body substantially aligned with an axis of said site portion of said impactor body, and said impactor portion and said impactor extension member configured to mate such that an impaction axis of said impactor body and an impaction axis of said extension member are substantially axially aligned.

2. The surgical retractor of claim 1, wherein said junction is bent.

3. A surgical retractor of claim 1, wherein said surgical retractor is sized and configured for use in minimally invasive hip procedures.

4. A surgical retractor of claim 3, wherein said handle portion is longer than said site portion in order to accommodate hip surgery procedures.

5. A surgical retractor of claim 4, wherein said handle portion is angled at about 110 degrees relative to said site portion in order to accommodate hip surgery procedures.

6. A surgical retractor of claim 1, wherein a cross-sectional width of said impactor portion of said impactor body is larger than a cross-sectional width of said support portion of said impactor body.

7. A surgical retractor of claim 1, wherein said impactor portion is configured to mate with said impactor extension member in a non-rotating relationship, such that about 5 or 6 degrees of freedom of motion are controlled at a junction of said impactor portion and said impactor extension member.

* * * * *